US009119747B2

(12) United States Patent
Knecht

(10) Patent No.: US 9,119,747 B2
(45) Date of Patent: Sep. 1, 2015

(54) METHOD FOR PRODUCING AN ABSORBENT DISPOSABLE INCONTINENCE DIAPER AND APPARATUS FOR CONDUCTING THE METHOD

(75) Inventor: Theresia Knecht, Aalen (DE)

(73) Assignee: Paul Hartmann Aktiengesellschaft, Heidenheim (DE)

( * ) Notice: Subject to any disclaimer, the term of this patent is extended or adjusted under 35 U.S.C. 154(b) by 968 days.

(21) Appl. No.: 13/260,574

(22) PCT Filed: Mar. 24, 2010

(86) PCT No.: PCT/EP2010/001827
§ 371 (c)(1),
(2), (4) Date: Sep. 27, 2011

(87) PCT Pub. No.: WO2010/112160
PCT Pub. Date: Oct. 7, 2010

(65) Prior Publication Data
US 2012/0028777 A1 Feb. 2, 2012

(30) Foreign Application Priority Data
Apr. 4, 2009 (DE) .......................... 10 2009 016 381

(51) Int. Cl.
*B31B 1/00* (2006.01)
*B32B 37/00* (2006.01)
(Continued)

(52) U.S. Cl.
CPC ..... *A61F 13/15699* (2013.01); *A61F 13/15723* (2013.01); *A61F 13/15756* (2013.01); *A61F 13/15804* (2013.01); *Y10T 156/1052* (2015.01)

(58) Field of Classification Search
CPC ........ B32B 37/00; B32B 37/02; B32B 38/00; B32B 38/04; B32B 38/10; B32B 38/18; B32B 1/00; A61F 13/15699; A61F 13/15756; A61F 13/15804; A61F 13/15723
USPC ......... 493/373–374, 393–394, 378–382, 386, 493/405, 408, 210, 223–224, 231, 493/343–347; 156/229, 250, 60, 264; 605/385.21
See application file for complete search history.

(56) References Cited

U.S. PATENT DOCUMENTS 7,008,497 B2 * 3/2006 Nakakado et al. ............ 156/229
7,438,779 B2 * 10/2008 Nakakado ..................... 156/164
(Continued)

FOREIGN PATENT DOCUMENTS

DE 10 2005 048 868 4/2007
EP 2 020 215 2/2009
(Continued)

*Primary Examiner* — Gloria R Weeks
*Assistant Examiner* — Justin Citrin
(74) *Attorney, Agent, or Firm* — Paul Vincent

(57) ABSTRACT

The invention relates to a method for producing an absorbent disposable incontinence diaper (2), having a main part (4) comprising an absorption element (12), comprising a front region (6) having front side longitudinal edges (26), a rear region (8) having rear side longitudinal edges (25) and a crotch region (10) arranged there between and placed between the legs of a user, and having rear side sections (20) joined to the rear region (8) and front side sections (22) joined to the front region (6) on both sides, which extend in a transverse direction (30) of the disposable incontinence diaper (2) beyond the side front and rear longitudinal edges (25, 26) of the main part (4) and are spaced apart from one another in a longitudinal direction (18) of the disposable incontinence diaper (2), the rear and front side sections (20, 22) being connectable detachably to each other in order to apply the disposable incontinence diaper (2), characterized in that for the purpose of contouring leg opening regions (38) on both sides of the disposable incontinence diaper (2), the rear side sections (20) and/or the front side sections (22) are formed by a severing operation of side section webs (44, 72) that are supplied endlessly and are contoured in the process, and an endlessly supplied main part web (40) is folded in transversely with respect to the plane of the web and transversely which respect to the machine direction (42) before the endlessly supplied side section webs (44, 72) are joined, in that the side section webs (44, 72) are then joined onto the main part web (40), the severing operation (52) covering the side section webs is then carried out on both sides, so that the combination comprising the main part web (40) and joined side section webs (44, 72) can then be accelerated in the machine direction (42) and unfolded in the process, wherein the front and rear side sections (20, 22) can be spaced apart from each other in the longitudinal direction (18).

12 Claims, 6 Drawing Sheets

(51) Int. Cl.
*B32B 27/20* (2006.01)
*A61F 13/15* (2006.01)

(56) References Cited

U.S. PATENT DOCUMENTS

2006/0059598 A1* 3/2006 Lohoff .............................. 2/69

2009/0198205 A1* 8/2009 Malowaniec et al. .... 604/385.23

FOREIGN PATENT DOCUMENTS

| WO | WO 2006/007226 | 1/2006 |
| WO | WO 2008/155618 | 12/2008 |
| WO | WO 2009/002235 | 12/2008 |

* cited by examiner

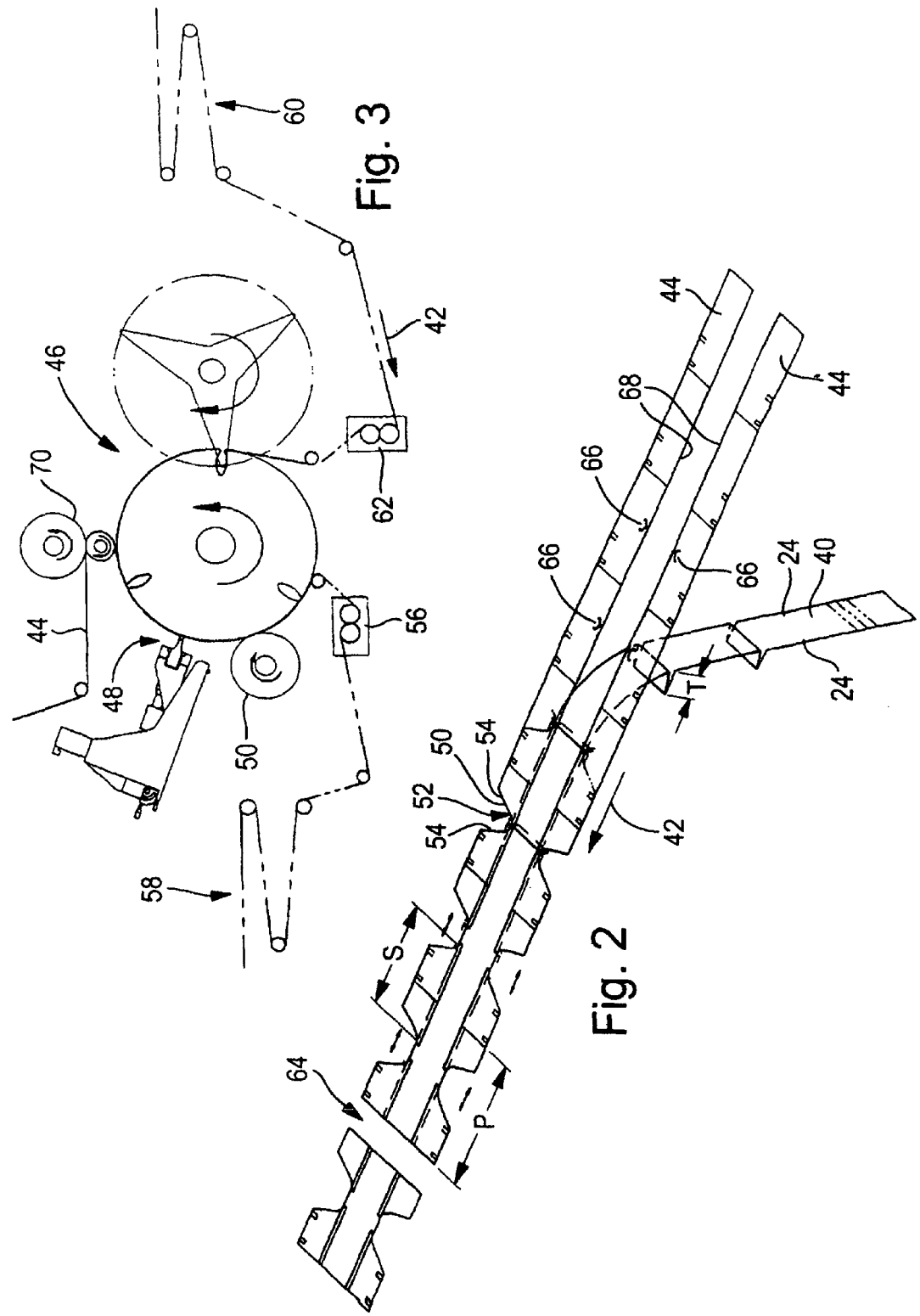

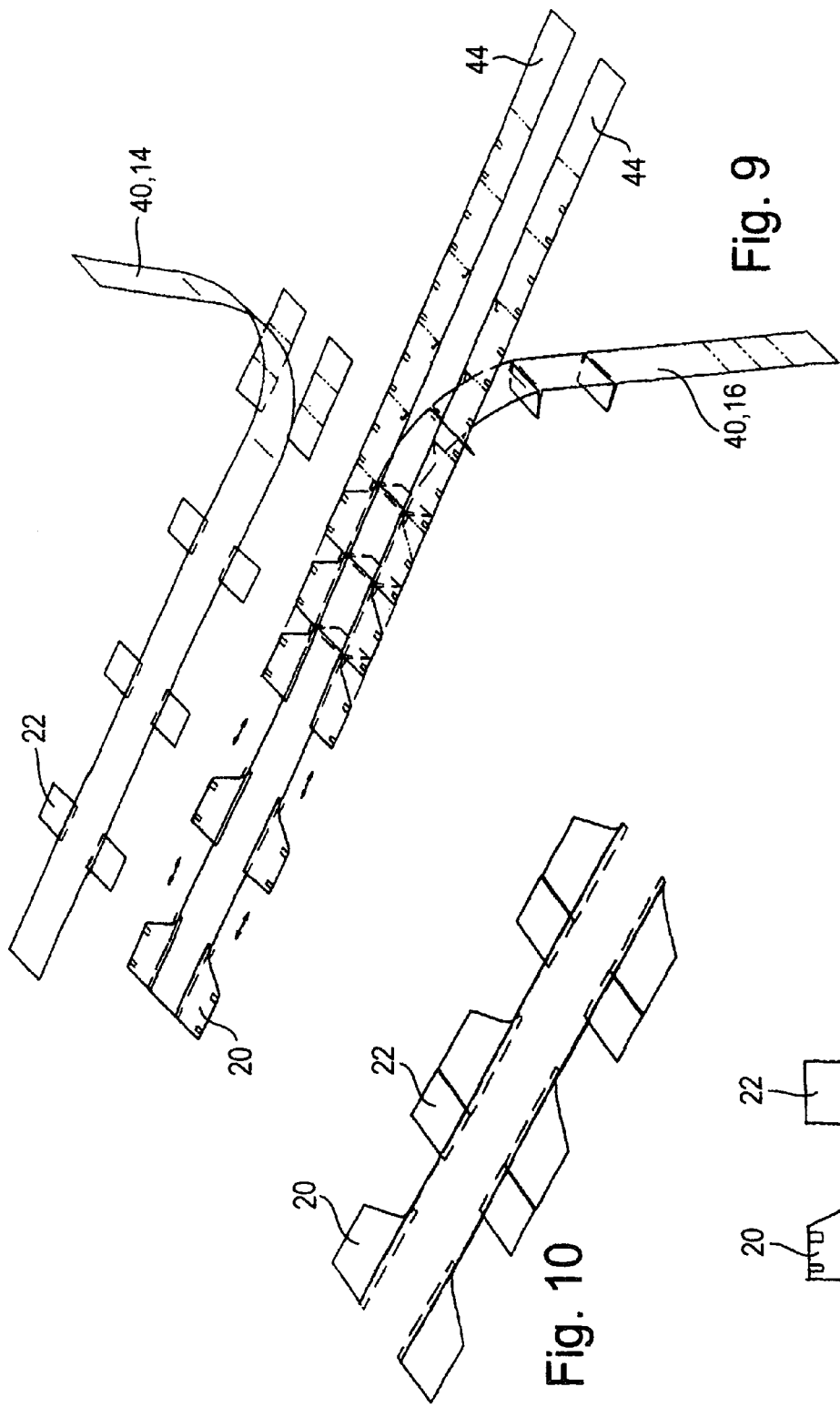

METHOD FOR PRODUCING AN ABSORBENT DISPOSABLE INCONTINENCE DIAPER AND APPARATUS FOR CONDUCTING THE METHOD

This application is the national stage of PCT/EP2010/001827 filed on Mar. 24, 2010 and claims Paris Convention Priority of DE 10 2009 016 381.6 filed Apr. 4, 2009.

BACKGROUND OF THE INVENTION

The invention concerns a method for producing an absorbent disposable incontinence diaper having a main part comprising an absorption element, and comprising a front region having front side longitudinal edges, a rear region having rear side longitudinal edges and a crotch region arranged therebetween and placed between the legs of a user, and having rear side sections joined to the rear region on both sides and front side sections joined to the front region on both sides, which extend in a transverse direction of the disposable incontinence diaper beyond the side front and rear longitudinal edges of the main part and are spaced apart from one another in a longitudinal direction of the disposable incontinence diaper, the rear and front side sections being detachably connectable to each other in order to apply the disposable incontinence diaper.

The above-mentioned side sections of disposable incontinence diapers of this type are often made from a different material than the main part. The side sections, which are also frequently called "ears" of the disposable incontinence diaper, may e.g. be designed to be breathable, in particular permeable to air and/or water vapor, whereas the main part, which is often also called the chassis, may be designed to be impermeable to liquid. For closing the disposable incontinence diaper, the side sections, which are preferably undetachably joined to the rear region, are folded to the belly side of the user, where they are detachably connected either to the outer side of the front region of the main part or to the outer side of the side sections of the front region.

It would e.g. be feasible to form the front and rear side sections by substantially rectangular sections of a sheet material, which are then applied in a cyclic fashion to a main part web forming the main parts of the diaper in a so-called cut-and-place method. In this case, the leg cut-outs, which are delimited by the longitudinal edges of the rear and front side sections, which face each other, and by a main part which has an, in particular, hourglass shape, are also delimited by straight edges which extend in a direction transverse to the machine direction, i.e. transversely with respect to the longitudinal direction of the disposable incontinence diaper. In contrast thereto, it is desirable for various reasons to provide the disposable incontinence diaper with contoured leg opening regions, which is hereby defined in that the edges of the rear side section and/or of the front side section delimiting the leg openings do not extend exactly in a transverse direction, i.e. not perpendicularly to the longitudinal direction of the diaper. It could comprise sections which extend e.g. in a straight line, however, at an angle with respect to the longitudinal direction of the disposable incontinence diaper and/or curved sections. In a preferred embodiment of the disposable incontinence diaper, the edge of the side sections delimiting the leg openings has exclusively curved, i.e. bent sections. The minimum curve radius is thereby advantageously at least 5 mm, in particular, preferably at least 10 mm. The contour of the leg opening regions advantageously comprises curved sections with a varying radius of curvature.

A method for producing such disposable incontinence diapers of the so-called open type is disclosed in EP 07 015 141.0 of the applicant.

It is therefore the object of the present invention to specify a method of the above-mentioned type which can be performed in an advantageous fashion in terms of process technology and with minimum expense in view of the cutting waste thereby produced.

SUMMARY OF THE INVENTION

In accordance with the invention, this object is achieved with a method of the above-mentioned type in that for contouring leg opening regions on both sides of the disposable incontinence diaper, the rear side sections and/or the front side sections are formed by a severing operation of endlessly supplied side section webs and are contoured in the process, and an endlessly supplied main part web is folded-in transversely with respect to the plane of the web and transversely with respect to the machine direction before the endlessly supplied side section webs are joined, the side section webs are then joined to the main part web, the severing operation covering the side section webs is then carried out on both sides so that the combination comprising the main part web and joined side section webs can then be accelerated in the machine direction and unfolded in the process, wherein the front and rear side sections can be spaced apart from each other in the longitudinal direction.

Due to the fact that the side section webs, which form the rear and/or front side sections, are supplied in an endless fashion and the mutually facing edges of the side sections are provided with a contour already during cutting off the relevant side sections from these endless side section webs, it is possible to realize stable process control under favorable technical process conditions, since the endless material webs can be processed until they are joined to the main part web. The further inventive measure of folding the main part web out of the plane of the web into a quasi inactive intermediate storage position allows endless supply of the side section webs on both sides and endless joining thereof to the main part web with the result that the cutting waste is substantially reduced at least almost to the degree which is absolutely unavoidable for contouring the edges of the side sections or of the leg opening regions of the diaper to be produced.

In one preferred process, the main part web is supplied and then folded out of the web plane, whereupon the side section webs are endlessly supplied on both sides and joined to the main part web. This is advantageously followed by the severing operation covering the side section webs, which has the function of a contour cut for contouring the mutually facing edges of the side sections or at least of a rear or front side section for forming contoured leg opening regions. The composite of main part web and joined and contoured side sections can subsequently be accelerated in the machine direction and thereby unfolded. This process of acceleration and unfolding is likely to be advantageous in most applications in view of subsequent configuration steps. However, it would basically also be at least feasible that the above-mentioned folding of the main part web remains and constitutes initial folding of the product for packaging purposes. The above-mentioned supply and folding of the main part web may also refer to a component of an endless web forming the subsequent main part such as e.g. an endless topsheet web or an endless backsheet web, which is then connected to further components forming the main part such as absorption element, distribution layer, topsheet (web), backsheet (web) etc. in accordance with the inventive process.

In accordance with a first embodiment of the inventive method, the rear and also the front side sections are formed on both sides by the same side section web. In this case, the depth of folding of the main part web is advantageously selected such that the length of the main part web available in the web plane for joining the side section webs of each disposable incontinence diaper corresponds to the length of the side sections of each disposable incontinence diaper. The folding depth in this case is 0.5×(product length−side section length), wherein the side section length is the sum of the extension in the longitudinal direction of the rear and front side sections in the machine direction. In this fashion, the overall crotch region of the main part web formed only by the main part web is thereby quasi folded away such that the side section webs can be utilized in an optimum economical fashion with respect to material with minimized cutting waste. After joining the side section webs and performing the severing operation covering the side section webs, i.e. the contour cut for providing a contour to the mutually facing edges of the side sections, the composite of main part web and side section webs can be unfolded again.

In accordance with a further embodiment of the inventive method, the respective front and rear side sections may be formed by different endlessly supplied side section webs, i.e. they may also comprise different materials. There are two variants.

In accordance with a first variant, a first side section web is joined to the previously folded main part web on both sides in a first application step and subsequently, a first severing operation covering the first side section webs is performed on both sides and the main part web is unfolded again. A second side section web is then joined on both sides to the previously again folded main part web in a second application step and subsequent thereto, a second severing operation covering the second side section webs is carried out on both sides. The fold of the main part web during the first application step and the fold of the composite of main part web and first side sections in the second application step is thereby larger than in the first embodiment, in which the main part web is only folded via the longitudinal extension of the crotch region into an inactive intermediate storage position. In the present case of the second embodiment of the inventive method, it has again turned out to be advantageous to select a maximum folding degree or folding depth such that the material of the relevant side section webs can be maximally utilized in the longitudinal direction of the machine, i.e. except for the cutting waste which cannot be avoided for providing the leg cut-outs with a contour.

In accordance with the second variant, in which the respective front and rear side sections are again formed by different side section webs, a first side section web is joined on both sides to a previously folded first component of the main part web, e.g. to an endless backsheet web, in a first application step, and a first severing operation covering the first side section webs is subsequently performed on both sides and the main part web is unfolded again. In a second application step which is performed, in particular, parallel to the first application step, a second side section web is joined on both sides to a previously folded second component of the main part web, e.g. to an endless topsheet web, and a second severing operation covering the second side section webs is subsequently performed on both sides and the main part web is unfolded again. The first and the second component of the main part web including the respective side sections are then conveyed on top of each other and connected to each other.

At this point, it should be specifically mentioned that the invention also includes disposable incontinence diapers of which only the rear or front side sections have a contour, i.e. the respective other side sections are joined with, in particular, rectangular material sections in the above-mentioned discontinuous cut-and-place method.

In accordance with a further embodiment of the inventive method which is of particular importance, a free cut is advantageously performed in the respective side section web in addition to the above-mentioned severing operation, which free cut extends to the respective inner edge of the respective side section web. Due to this free cut, the actual severing operation, i.e. the actual contour cut for forming the contour of the leg cut-outs, does not have to cover the overall width of the respective side section web. However, the free cut extending towards the edge ensures that the front and rear side sections are really separated and can be easily spaced apart from each other for unfolding after the severing operation.

In view of process technology, it has turned out to be particularly advantageous for the above-mentioned free cut to be performed in the endless side section web prior to joining to the main part web.

In a further embodiment of the invention, the free cut advantageously has a shape expanding from the inner edge of the side section web, in particular, a Y- or V-shape or the shape of a curly bracket. This method variant ensures, in a technically particularly elegant fashion, that, during the severing operation, the respective side section web is separated over its entire length, i.e. is cut, namely also in the region of the folding of the main part web where it may not be possible to always provide sufficient counter pressure of the cutting components.

In accordance with a further method variant, the main part web is guided over one single rotary body during folding, joining to the side section webs and performing the severing operation.

During folding of the endlessly supplied main part web, the main part web must be supplied with a speed curve which must be correspondingly calculated, i.e. with a cyclically varying speed. This is advantageously realized in that the speed curve is performed using a compensator arrangement provided upstream of the folding process and correspondingly downstream of the unfolding process. The compensator arrangement forms a storage for the web length that is additionally required for folding or for the web length that must be additionally discharged during unfolding.

A device for producing disposable incontinence diapers is also subject matter of the invention as recited in the respective dependent claims.

Advantageous sizes of the disposable incontinence diaper are stated below:

The length of the side sections, i.e. their extension in the longitudinal direction of the diaper is advantageously at least 15 cm, in particular at least 20 cm, moreover, in particular at least 25 cm. It has moreover turned out to be advantageous for the length of the side sections to be at least 10%, in particular at least 15%, and moreover, in particular at least 20%, and moreover, in particular at least 22%, however, at most 40%, and moreover, in particular at most 35% of the overall length of the disposable incontinence diaper. The overall length of the disposable incontinence diaper is advantageously 50 to 120 cm, in particular 60 to 110 cm and moreover in particular 70 to 110 cm. It has moreover turned out to be advantageous for the front side sections to have a smaller extension in the longitudinal direction than the rear side sections, in particular by at least 5%, moreover in particular at least 10%, moreover in particular at least 15%, and moreover in particular at most 50%. In a further development of the invention, the width of the side sections, i.e. the extension of the side sections beyond the side edge of the diaper main part is 10 to 45 cm, in particular 13 to 35 cm, moreover in particular 15 to 27 cm. The front side sections advantageously have the same width as the rear side sections. In a further development of the invention, the rear side sections advantageously have a larger surface extension (measured in cm$^2$) preferably by at least 10%, in particular at least 15%, than the front side sections.

It has furthermore turned out to be advantageous for the front and/or rear side sections to be formed from or comprise a non-woven material, since these three-dimensional non-woven materials, which are rather voluminous and lofty compared to foils, are suited to be discharged from the process in the form of cutting waste as explained in accordance with the invention.

The non-woven materials may contain fibers of PE, PP, PET, Rayon, Cellulose, PA and mixtures of these fibers. Bi or multi-component fibers are also feasible and advantageous. Advantageous are, in particular, card webs, spunbonded non-woven materials, water-jet-needled non-woven materials, SM nonwoven materials, SMS non-woven materials, SMMS non-woven materials or also laminates of one or more of these non-woven materials, wherein S stands for spunbond and M for meltblown non-woven materials.

The main part web advantageously comprises a non-woven material and/or an absorption element material and/or a backsheet material. The backsheet material may, in particular, be a foil material or a liquid-impermeable non-woven material or a non-woven/foil laminate.

Further features, details and advantages of the method and the device in accordance with the invention can be extracted from the following claims and the drawing and the following description of preferred embodiments of the invention. In the drawing:

BRIEF DESCRIPTION OF THE DRAWING

FIG. 2 shows a schematic view of the supply, folding, joining, severing, and unfolding processes in accordance with the inventive method;

FIG. 3 shows a schematic view of an inventive device for performing the production method in accordance with the invention;

FIG. 9 shows a schematic view of the processes according to a further embodiment of the inventive method, in the course of which only the rear side sections are contoured; and FIG. 10 shows the composite of main part web with rear and front side sections in accordance with the method of FIG. 9;

FIG. 11 shows a top view of a singled disposable incontinence diaper obtained in accordance with the method of FIGS. 9 and 10.

DESCRIPTION OF THE PREFERRED EMBODIMENT

Figure 1:
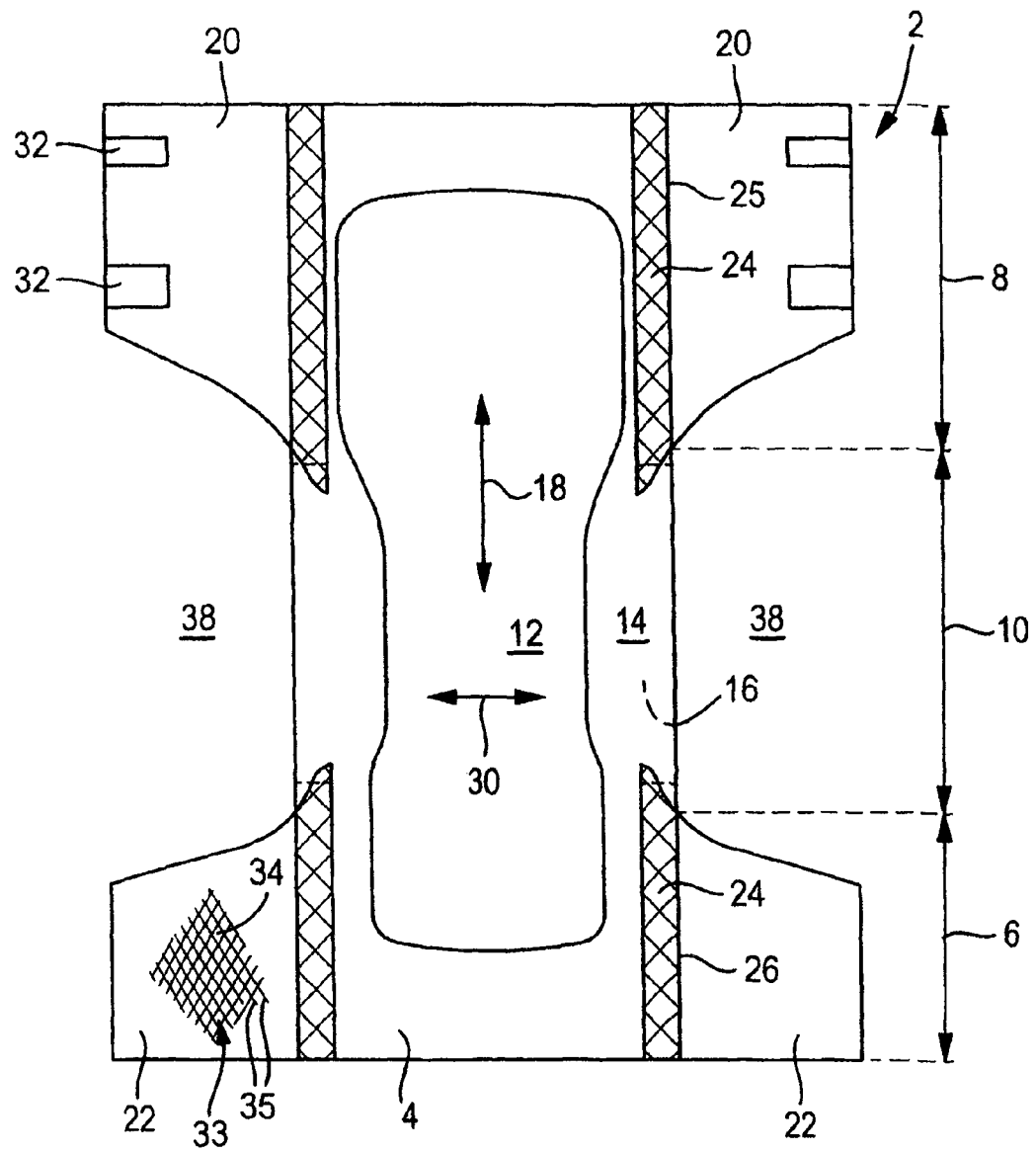
FIG. 1 shows a schematic top view of a disposable incontinence diaper being produced.

FIG. 1 schematically shows a top view of an inner side, i.e. a side of an absorbent disposable incontinence diaper 2 facing the body which can be opened and closed, in a flat unfolded state. The disposable incontinence diaper 2 comprises a main part 4 with a front region 6, a rear region 8 and a crotch region 10 disposed therebetween in the longitudinal direction. An absorption element 12 is also indicated, which is normally disposed between chassis-forming materials of the main part 4, i.e. in particular between a liquid-permeable topsheet 14 formed from a non-woven material and a substantially liquid-impermeable backsheet 16, formed from foil material, of the main part 4. The backsheet 16 may also be formed from a liquid-impermeable non-woven material or a non-woven/foil laminate, wherein the non-woven layer then comes to rest on the outside and the foil layer on the inside facing the absorption element. This gives the disposable incontinence diaper 2 a textile impression. Elastic elements, which are not shown, are joined to the main part 4, in particular between the topsheet 14 and the backsheet 16 on the side next to the longitudinal edges of the absorption element 12. The elastic elements substantially extend in the longitudinal direction 18 of the disposable incontinence diaper, i.e. with a substantial component in the longitudinal direction 18, wherein they may extend in a curved fashion along the section of the leg openings to be associated with the crotch region 10.

The disposable incontinence diaper 2 moreover comprises rear side sections 20 and front side sections 22 which are joined as non-woven material components on both sides to the main part 4. The side sections 20, 22 are advantageously joined to the main part 4 using ultrasound welding. The side sections 20, 22 are undetachably connected in a hatched side edge region 24 to chassis-forming materials of the main part 4, i.e. for example to the backsheet 16 and/or the topsheet 14. The side sections 20, 22 extend in a transverse direction 30 beyond the front and rear longitudinal edges 25, 26 of the main part 4. The rear side longitudinal edges 25, 26 of the main part 4 delimit those longitudinal edge regions of the main part to which the side sections 20, 22 are joined and beyond which the side edge sections 20, 22 extend in the transverse direction. The longitudinal extension of the front and rear longitudinal edges 25, 26 of the main part 4 thereby also defines the longitudinal extension of the front region 6 and of the rear region 8 of the main part 4 and also of the disposable incontinence diaper as illustrated in FIG. 1. The side sections 20, 22 are devised and designed to be connected to each other when the disposable incontinence diaper 2 has been applied in order to form a hygiene article hip region which is continuous in the peripheral direction. The side sections 20, 22 that are provided on each side of the main part 4 are thereby connected to each other. Towards this end, mechanical closure means 32, in particular, comprising mechanical closing aids such as hooks, are provided on the rear side sections 20, which can be detachably fixed to the outer side of the front side sections 20, 22. The closure means 32 can moreover also be detachably fixed to the outer side of the main part 4. Both the front side sections 22 and the rear side sections 20 are formed from a non-woven material, in the exemplary case, of a PP spunbonded non-woven material. The surface density of the non-woven material of the front side sections 22 is 30 g/m$^2$. The fiber thickness of the fibers forming the non-woven material is 2 dtex. The outer and inner sides of the non-woven material have an embossed pattern 33 which is only indicated in FIG. 1. The joining regions of the embossed pattern 33 generated by hot calender embossing are formed by a plurality of embossed lines 35, namely by two groups of embossed lines 35 which extend parallel to each other within each group, wherein the embossed lines of one group intersect the embossed lines of the other group for forming a regular diamond-shaped pattern at an angle of, for example, 33 degrees such that diamond-shaped loop regions 34 that are arranged like islands are surrounded by embossed lines 35. In the illustrated case, the embossed lines 35 have a width of 1.0 mm and an embossed depth of 0.6 mm. The separation between neighboring parallel extending embossed lines 35 of both groups of lines is 4.7 mm. The embossed surface, i.e. the sum of the surface of all embossed lines 35 relative to the overall surface of the embossed pattern (embossed lines 35+loop regions 34) is 32%. The closure means 32 of the rear side sections 20 can be reliably brought into engagement with these loop regions 34. The forces that retain the diaper on the belly between the closure means 32 and the outer side of the front side sections 22 are advantageously at least 58 N/25 mm.

In the illustrated case, the surface density of the non-woven material of the rear side sections 20 is 25 g/m². An embossed pattern forming loop regions and joining regions is not provided. The forces between the closure means 32 and the outer side of the rear side sections 20, which retain the diaper on the belly, are therefore smaller than the forces acting between the closure means 32 and the outer side of the front side sections 22. They are preferably nevertheless at least 15 N/25 mm measured according to the test method described in EP 1915977 A1. As can be gathered from FIG. 1, the rear side sections 20 moreover have a larger surface extension than the front side sections 22.

The front and rear side sections 20, 22 therefore differ with respect to at least three of their primary characteristics, i.e. the surface density, the closing force and the surface extension. The difference in the closing force between the front and rear side sections causes the user to preferably fix the closure means 32 to the front side sections 22, which is beneficial for a good fit of the diaper. As can be further gathered from FIG. 1, leg opening regions 38 are formed by front and rear side sections 20, 22 which are curved towards the crotch region 10. An hourglass shaped contour of the main part 4 would additionally also be feasible. An hourglass shaped contour of the main part 4 thereby means any form of narrowing of the main part 4 in the crotch region 10, in which the crotch region 10 of the main part 4 has a smaller extension in the transverse direction 30 than the front region 6 and/or the rear region 8 of the main part.

The method in accordance with the invention for producing the above-described disposable incontinence diaper is explained in more detail below:

FIG. 2 schematically shows the different steps, which are in the main focus of interest in the present case, for producing the inventive disposable incontinence diaper 2. A main part web 40 and also two side section webs 44, which form the subsequent rear and front side sections 20, 22 on both sides, are endlessly supplied in the machine direction 42. The main part web 40 is folded transversely to the machine direction 42 and transversely to the web plane (shown in the device 46 in FIGS. 3 and 4) prior to application and joining of the side section webs 44 to the side edge regions 24 of the main part web. The folding depth T is thereby selected in such a fashion that substantially the entire length of the subsequent crotch region 10 is folded away from the web plane. The folding depth T is thereby 0.5×(product length P−side section length S). The side section webs 44 are then applied to the main part web 40 on both sides and undetachably connected to the main part web 40 by passing an ultrasound sonotrode 48 in the machine direction 42 in a substantially continuous fashion (even when individual welding joints are used for this purpose). This is followed by a severing operation, in which a contour cut 52 is performed in the side section webs 44 by means of a cutting roller 50, thereby providing the edges 54 of the side sections 20, 22 with a contour and also separating the side sections 20, 22 in the region of the contour cut 52.

The composite of main part web 40 and side section webs 44 is then accelerated using a removal device 56 and is thereby unfolded. The crotch region 10 is thereby moved back to the web plane and the rear and front side sections 20, 22 are spaced apart from each other again. A compensator arrangement 58 is disposed downstream thereof for receiving this folded length. A corresponding compensator device 60 and supply device 62 are disposed upstream of the above-described process.

FIG. 2 moreover indicates the step 64 of singling the disposable incontinence diapers 2.

The cutting waste from the side section webs 44 produced by contouring the mutually facing edges 54 of the rear and front side sections 20, 22 can be reduced to a minimum degree by the inventive process of folding the main part web 4. It is nevertheless possible to work with endless side section webs 44, which is advantageous in terms of process technology.

Reference is also made to a further particularly advantageous method detail: a free cut 66, which has e.g. the shape of a curly bracket, is provided in the endless side section webs 44 preferably prior to application to side edge regions 24 of the main part web 4, the free cut extending up to the mutually facing inner longitudinal edges 68 of the side section webs 44. In this fashion, the severing operation in the form of the contour cut 52 need not be extended to the longitudinal edges 68 and therefore into the overlapping region with the main part web 40 but must merely extend to this free cut 66 in order to ensure proper separation of the rear and front side sections 20, 22 and therefore ensure that the composite of main part web 40 and side section webs 44 can be unfolded. In the preferred example, this free cut 66 is designed in such a fashion that it widens starting from the longitudinal edges 68. It could also be V-shaped or Y-shaped or widen in any other shape in order to safeguard the advantage in accordance with the invention. It is, however, basically also possible to provide slits that are open towards the longitudinal edge 68 in the side section webs 44 for the intended purpose. It has turned out, however, that it is possible to realize stable and reliable separation in terms of process technology of the rear and front side sections 20, 22 by the widening shape of the free cut 66 even when the counterpressure for the cutting roller 50 in the region where the main part web is folded (in the apex of the contour cut 52) is possibly not sufficient. In the present example, the above-mentioned free cut 66 is performed by a cutting device 70. The free cut could also be realized by cutting or punching out an, in particular, round or oval flat piece.

Figures 5, 6:
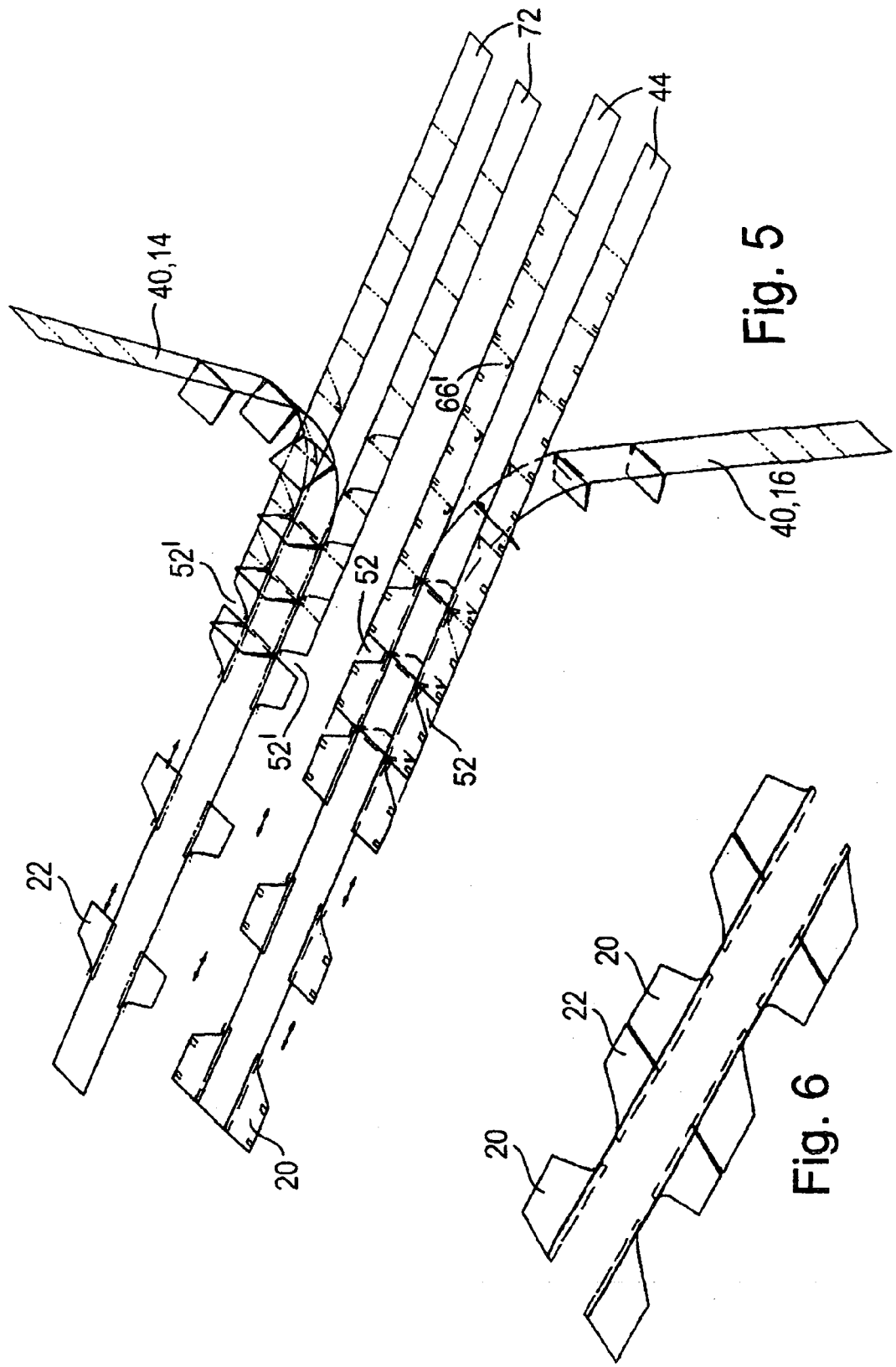
FIG. 5 shows a schematic view of the production processes according to a further embodiment of the inventive method.
FIG. 6 shows the composite of main part web and contoured side sections according to the method of FIG. 5.

FIGS. 5 and 6 show a further embodiment of the inventive method, in which the rear and front side sections 20, 22 are formed by different side section webs, namely the rear side sections 20 are formed by first side section webs 44 on both sides and the front side sections 22 are formed by second side section webs 72 on both sides. The main part web is again designated with reference numeral 40. It comprises, however, only one component in the form of the backsheet 16 as endless backsheet web. In a first application step, this component is endlessly supplied to the main part web 40 and folded with a folding depth which is larger than in the first embodiment, such that its length that remains in the web plane corresponds to the length of the rear side sections 20 (per product). The first side section webs 44 are then supplied as illustrated in FIG. 5 and are undetachably fixed to the side edge regions 24 in correspondence with the first embodiment. The contouring, i.e. the severing operation, is then performed in the form of a corresponding contour cut 52 in the side section webs 44 and the composite of main part web 40 and side section webs 44 is unfolded.

In particular, parallel to this, a further component of the main part web 40 is supplied in the form of the topsheet 14 as endless topsheet web and is correspondingly folded (as illustrated at the top in FIG. 5 by way of example) such that in this case, the length remaining in the web plane per product corresponds to the length of the front side sections 22. The two side section webs 72 are subsequently supplied on both sides and undetachably applied, which is followed by performing a further contour cut 52', followed by unfolding. The two webs are then guided on top of each other and connected to each other, wherein an absorption element (not shown) may be disposed between the topsheet web and the backsheet web. The web has then the shape as illustrated in FIG. 6.

In contrast to the first embodiment, the respective front side sections 22 are already separated from the directly bordering rear side sections 20 of the neighboring product even before the individual products are singled.

Figure 4:
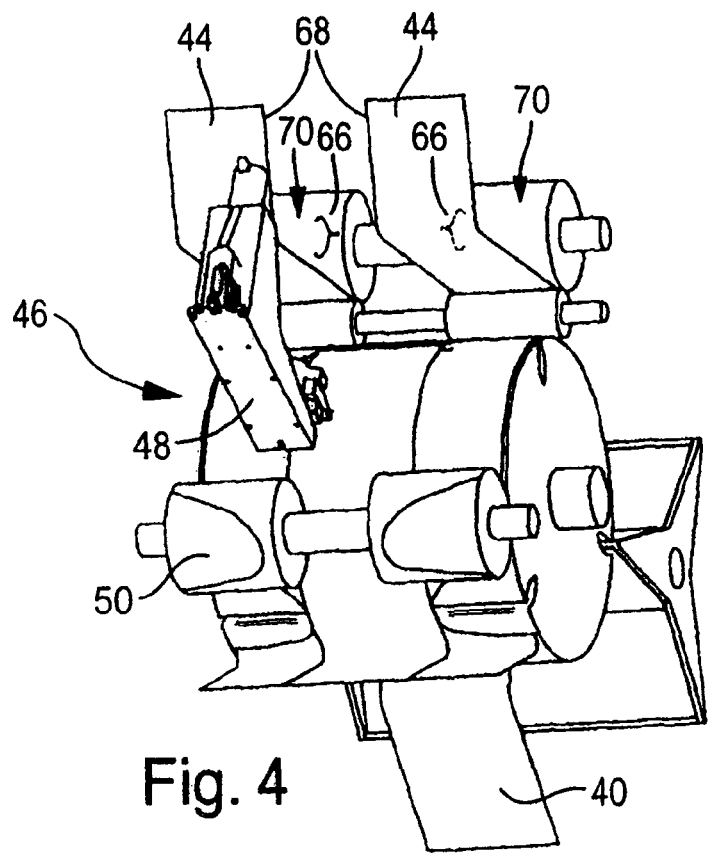
FIG. 4 shows a perspective view of the device according to FIG. 3.
Figure 8:
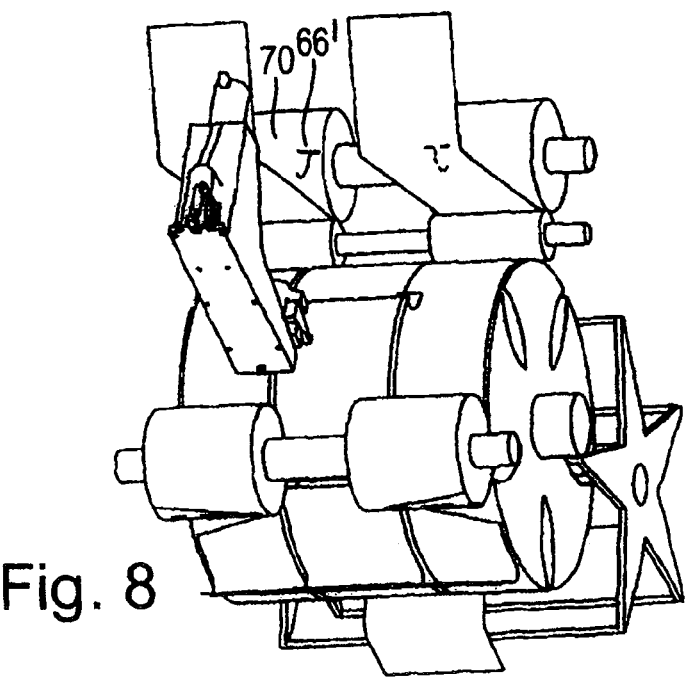
FIGS. 7 and 8 show views of a device for performing the method in accordance with FIGS. 7 and 8.
Figure 7:
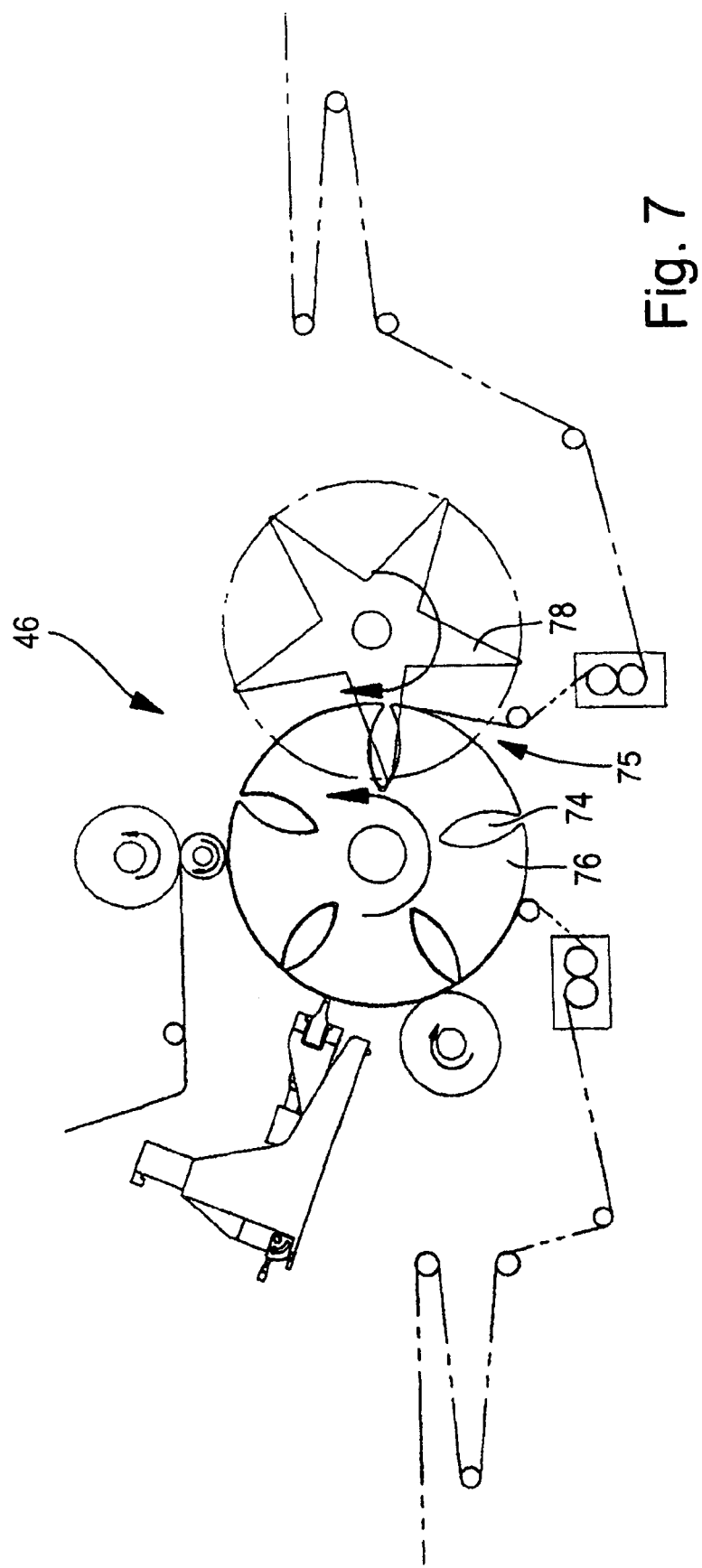

FIGS. 7 and 8 show a device 46 that basically corresponds to FIGS. 3 and 4, for performing the method, comprising folding openings 74 of a folding device 75, having a first rotary body 76 and a rotating displacing element 78 of the device 46 for corresponding deeper folding of the main part web 40. The free cutting device 70 moreover has the shape of a knife (shown in FIG. 8) for forming a suitable free cut 66' which also has a shape that widens only on one side.

FIGS. 9 through 11 illustrate a further variant of the inventive method, wherein only the respective rear side sections 20 are formed by supplying and applying endless side section webs 44 to a previously folded component (e.g. backsheet web) of the main part web 40. The respective front side sections 22 are attached and undetachably fixed to another component (e.g. topsheet web) of the main part web 40 in a cyclic fashion using the cut-and-place method.

I claim:

1. A method for producing an absorbent disposable incontinence diaper, the diaper having a main part comprising an absorption element, a front region with front side longitudinal edges, a rear region having rear side longitudinal edges and a crotch region disposed between the front region and the rear region for placement between legs of a user, the diaper further comprising rear side sections joined to the rear region on both sides thereof as well as front side sections joined to the front region on both sides thereof, the front and rear side sections extending in a transverse direction of the disposable incontinence diaper beyond the respective front and rear side longitudinal edges of the main part and being spaced apart from one another in a longitudinal direction of the disposable incontinence diaper, wherein the rear and front side sections are structured for detachable connection to each other in order to apply the disposable incontinence diaper, the method comprising the steps of:
  a) endlessly supplying a main part web and side section webs;
  b) folding the main part web transversely to a plane defined by a top surface of the main part web and transversely with respect to a machine direction;
  c) joining, following step b), the side section webs to the main part web;
  d) severing, following step c), the side section web for contouring leg opening regions on both sides of the disposable incontinence diaper; and
  e) accelerating, following step d), the main part web and joined side section webs in the machine direction, thereby unfolding the main part web and spacing apart, in the longitudinal direction of the diaper, front and rear side sections fashioned from the side section webs.

2. The method of claim 1, wherein a depth of a fold of the main part web generated in step b) is selected such that a length of the main part web available in the plane defined by the top surface of the main part web for joining the side section webs of each disposable incontinence diaper corresponds to a length of side sections of each disposable incontinence diaper.

3. The method of claim 1, wherein respective front and rear side sections are formed by different endlessly supplied side section webs, a first side section web thereby being joined on both sides to a previously folded first component of the main part web in a first application step, and a first severing operation being subsequently performed on both sides of the first side section webs and the main part web is then unfolded, wherein, in a second application step, a second side section web is joined on both sides to a previously folded second component of the main part web and a second severing operation is applied to the second side section webs on both sides thereof, the main part web is then unfolded, and the first and the second components of the main part web, with the joined respective side sections, are conveyed on top of each other and are connected to each other.

4. The method of claim 3, wherein the second application step is performed in parallel to the first application step.

5. The method of claim 1, wherein front and rear side sections are formed by different side section webs in that, in a first application step, rear or front side sections are joined to both sides to the main part web using a cut-and-place method, and, in a second application step, an endlessly supplied side section web is joined on both sides to a previously folded main part web, followed by a severing operation applied to the side section webs on both sides thereof.

6. The method of claim 5, wherein in the first application step, rear or front side sections are joined in the cut-and-place-method to a first component of the main part web, and the main part web is then unfolded, and, in a second application step, an endlessly supplied side section web is joined on both sides to a previously folded second component of the main part web and subsequent thereto, a severing operation is applied to both sides of the side section webs on the main part web, the main part web is unfolded, and the first and the second components of the main part web, with the respective side sections, are conveyed on top of each other and are connected to each other.

7. The method of claim 1, wherein, in addition to the severing operation of step d), a free cut is applied to a respective side section web, the free cut extending to a respective inner edge of the respective side section web.

8. The method of claim 7, wherein the free cut is formed in an endless side section web prior to joining to the main part web.

9. The method of claim 7, wherein the free cut has a shape which widens from an inner edge of the side section web.

10. The method of claim 9, wherein the free cut has a substantially Y- or V-shaped form or a shape that corresponds to a curly bracket.

11. The method of claim 1, wherein the main part web is guided over one single rotary body during folding, joining to the side section webs and performing of the severing operation.

12. The method of claim 1, wherein one upstream and/or one downstream compensator arrangement is used during a folding and/or unfolding action.

* * * * *